United States Patent [19]

Knox

[11] Patent Number: 5,081,306
[45] Date of Patent: Jan. 14, 1992

[54] SYNTHESIS OF DIHALOBENZENE DISULFONE COMPOUNDS

[75] Inventor: David E. Knox, Matawan, N.J.

[73] Assignee: Amoco Corporation, Chicago, Ill.

[21] Appl. No.: 538,988

[22] Filed: Jun. 15, 1990

Related U.S. Application Data

[63] Continuation of Ser. No. 342,922, Apr. 25, 1989, abandoned, which is a continuation of Ser. No. 798,981, Nov. 18, 1985, abandoned.

[51] Int. Cl.$^5$ .......................... C07C 281/00
[52] U.S. Cl. ........................................ 568/34
[58] Field of Search ............................ 568/34

[56] References Cited

U.S. PATENT DOCUMENTS 4,871,876 10/1989 Schaefer et al. .................. 568/34

Primary Examiner—Mary C. Lee
Assistant Examiner—Robert C. Whittenbaugh
Attorney, Agent, or Firm—William H. Magidson; Ralph C. Medhurst

[57] ABSTRACT

A process for producing dihalobenzene disulfone compounds, comprising reacting, in the presence of aluminum trichloride
a halobenzene sulfonyl halide of the formula

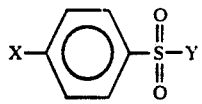

wherein X and Y are halogen which may be the same or different, with
a compound of the formula

H - Q - H wherein Q is a divalent radical containing benzenoid unsaturation and the hydrogens are replaceable under electrophilic Friedel-Crafts reaction conditions,
in a solvent consisting essentially of about 1 to about 25 volume %, based on the solvent volume, of nitromethane and, correspondingly, about 99 to about 75 volume %, of a polar aliphatic halohydrocarbon, the total solvent volume employed being sufficient to provide between about 0.5 and about 1.5 moles of nitromethane per mole of aluminum trichloride,
thereby producing a dihalobenzene disulfone compound of the formula

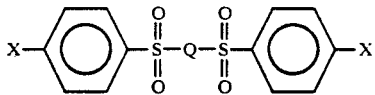

6 Claims, No Drawings

SYNTHESIS OF DIHALOBENZENE DISULFONE COMPOUNDS

This is a continuation of application Ser. No. 07/342,922, filed Apr. 25, 1989, now abandoned, which in turn is a continuation of application Ser. No. 06/798,981, filed Nov. 18, 1985, now abandoned.

FIELD OF THE INVENTION

This invention relates to an improved method of synthesizing, in a mixed solvent system, a select class of dihalobenzene disulfone compounds useful as monomers for the production of poly(aryl ether sulfones).

BACKGROUND OF THE INVENTION

The use of dihalobenzene disulfone compounds to make poly(aryl ether sulfones) generally is known to the art. See U.S. Pat. Nos. 3,647,751 to Darsow; 3,960,815 to Darsow et al.; 4,009,149 to King et al.; 4,056,511 to Staniland; and 4,105,635 to Freeman, for example. These patents generally disclose making poly(aryl ether sulfones) wherein some of the polymers disclosed therein are made using compounds of the Formula

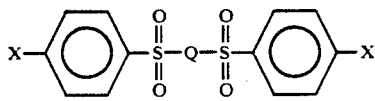

wherein X is halogen and Q is a divalent benzenoid moiety such as phenylene, biphenylene, biphenylene ether, terphenylene, and the like.

The Friedel Crafts catalyzed synthesis of dihalobenzene disulfone compounds themselves has been variously described in the patent and technical journal literature. U.S. Pat. No. 4,303,776 to Baron et al. discloses the ferric chloride synthesis of 4,4'-bis(4-chlorophenyl sulfonyl) biphenyl from biphenyl and 4-chlorobenzene sulfonyl chloride (pCBSC) wherein the pCBSC apparently is used as both a reactant and a solvent. The patent states that a 45% conversion was obtained after purification. Cornell et al., Soc. Plas. Eng. Tech. Papers, 21, 621-623 (1975) disclose virtually the same synthesis on a laboratory scale and report scaled up large reactor yields in excess of 80% when the reaction is run in nitrobenzene (a conventional solvent for Friedel-Crafts reactions) and a temperature schedule gradually increasing from 70° C. to 130° C. is employed. The use of nitrobenzene as a solvent is commercially unattractive, however, due to its high toxicity, a Permissible Exposure Limit of only 1 part per million being allowed in the workplace (NIOSH/OSHA Pocket Guide To Chemical Hazards, Govt. Printing Office, September, 1978).

Mixed solvent systems have been disclosed for use with some Friedel-Crafts polymerization systems. International application number PCT/US84/00465 (Raychem Corporation), published Oct. 11, 1984 under publication number WO 84/03891 discloses an improved electrophilic synthesis of poly(arylene ketones) in a reaction medium comprising a Lewis acid (i.e., a Friedel-Crafts catalyst), a Lewis base, and a non-protic diluent. A large number of Lewis bases are disclosed, including nitro compounds of which nitropropane and nitrobenzene are specifically cited. Diluents mentioned include methylene chloride and dichloroethane. The applicant states that the Lewis acid complexes with the Lewis base, and that the complex appears to act as a solvent for the polymer-Lewis acid complex formed during the reaction thereby maintaining the polymer in solution or in a reactive gel state. The applicant states that the reaction mixture is more tractable to work up and believes that the solubilization of the polymer by the Lewis acid/Lewis base complex aids in achieving high molecular weight.

A. Fritz, in Poly. Prepr., Am. Chem. Soc., Div. Polym. Chem., 12(1), 232-239, (March 1971), discloses that the Friedel-Crafts condensation of aromatic isopropylchlorides with aromatic compounds can be adapted to polymer formation. The article states that it was necessary to solvate the Lewis acids with nitro compounds such as nitrobenzene or nitroalkanes in order to yield high molecular weight products. It was also stated to be essential to use metathetic catalysts in order to prevent reversibility and indane formation. Solvents disclosed included chloromethane, methylene chloride, chlorobenzene, dichlorobenzene, and dichloroethane.

Mixed solvent systems have also been disclosed in the patent literature in reaction systems which are far removed from those of the above publications. Thus U.S. Pat. No. 4,053,517 to Reininger et al., for example, discloses the Friedel-Crafts acylation of phloroglucinol wherein the acylation is conducted in a solvent system composed of nitromethane and methylene chloride.

THE INVENTION

The present invention provides a process for producing dihalobenzene disulfone compounds, comprising reacting, in the presence of aluminum trichloride, a halobenzene sulfonyl halide of the formula

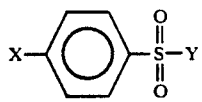

wherein X and Y are halogen which may be the same or different, with a compound of the formula

H-Q-H wherein Q is a divalent radical containing benzenoid unsaturation and the hydrogens are replaceable under electrophilic Friedel-Crafts reaction conditions, in a solvent consisting essentially of about 1 to about 25 volume %, based on the solvent volume, of nitromethane and, correspondingly, about 99 to about 75 volume % of a polar aliphatic halohydrocarbon, the total solvent volume employed being sufficient to provide between about 0.5 and about 1.5 moles of nitromethane per mole of aluminum trichloride, thereby producing a dihalobenzene disulfone compound of the formula

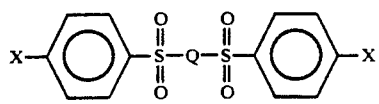

The invention particularly features using a mixed solvent system consisting essentially of nitromethane and an aliphatic halohydrocarbon in the proportions specified to produce a select class of compounds by electrophilic Friedel-Crafts synthesis. Conducting the reaction using the mixed solvent system permits obtaining the dihalobenzene disulfone monomer as polymer grade material and, importantly, as a high quality pure white or very light yellow product following recrystallization. This is surprising since conducting the reaction using an amount of nitromethane or an amount of an aliphatic halohydrocarbon, both of which are conventional solvents for Friedel-Crafts reactions, outside the volume range specified, including either pure nitromethane or pure halohydrocarbon, generally results in a product of poor color quality. Employing an amount of nitromethane much greater than about 25 volume % of the mixed solvent yields a brown product which is frequently "sludgy" due to the formation of tars. In addition, the use of nitromethane in large volume percentages is undesirable due to higher solvent cost and to the instability of nitromethane (e.g. nitromethane can be used as rocket fuel). Using an amount of nitromethane much less than about 1 volume % of the mixed solvent similarly results in a brown product. Such poor color frequently persists even after recrystallization.

The invention also permits obtaining greater yields of disulfone product than those obtained in a halobenzene sulfonyl halide, i.e., where the halobenzene sulfonyl halide is employed as both a reactant and a solvent.

A volume of mixed solvent is employed which will provide between about 0.5 and about 1.5 moles, preferably between about 0.75 and about 1.25 moles, and most preferably between about 0.85 and about 1.05 moles of nitromethane per mole of catalyst.

H-Q-H is a Friedel-Crafts substrate having benzenoid unsaturation and two benzenoid (i.e., attached directly to a benzene ring) hydrogens which may be replaced under the electrophilic Friedel-Crafts reaction conditions employed. The hydrogens occur on different benzene rings. It is preferred that the rings containing the replaceable hydrogens not be substituted with electron withdrawing groups which deactivate the ring to electrophilic attack. Suitable "Q" moieties (i.e. the moieties remaining after removal of the two replaceable hydrogens from QH$_2$) include:

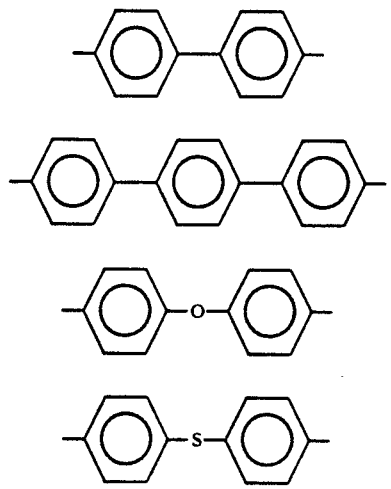

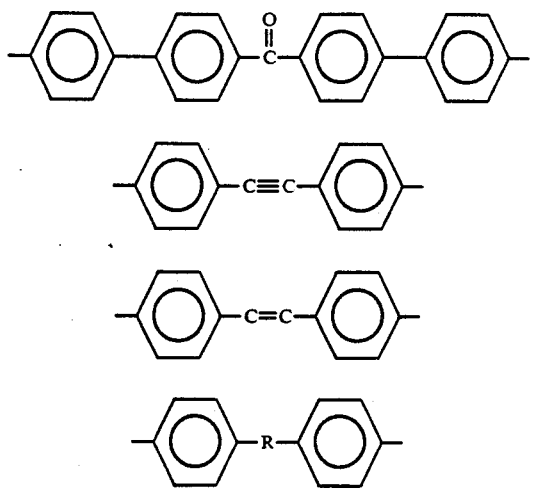

wherein R is an aliphatic linking group of up to about 6 carbon atoms such as —CH$_2$—, CH$_2$—CH$_2$—,

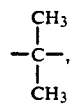

and the like.

As halobenzene sulfonyl halide (also referred to herein as a "sulfonylating agent"), p-chlorobenzene sulfonyl chloride (pCBSC) and p-fluorobenzene sulfonyl chloride are preferred.

Suitable polar aliphatic halohydrocarbon mixed solvent components include tetrachloroethane, trichloroethane, dichloroethane, and the like. Dichloroethane is preferred. The fluorinated analogs may be used although chlorohydrocarbons are preferred due to their inexpensiveness. Non-polar halogenated hydrocarbons such as carbon tetrachloride are not useful and "polar" is meant to exclude such solvents which do not have a permanent dipole moment. Although polar aliphatic solvents such as methylene chloride may be employed, such low boiling solvent components are not preferred due to the low reaction temperature they effect in the mixed solvent which results.

Polar aromatic halohydrocarbons such as ortho dichlorobenzene are in general not suitable for use in this invention as mixed solvent components because the resulting dihalobenzene disulfone product has poor color quality relative to using the pure halohydrocarbon as solvent.

As Friedel-Crafts catalyst aluminum trichloride is used. Aluminum chloride is advantageous particularly if low grade halobenzene sulfonyl halide (HBSH) which has not been extensively purified is employed. The solubility of the dihalobenzene disulfone monomer product is also better in reaction solutions containing aluminum trichloride, thus making workup easier. The amount of aluminum chloride typically varies between about 1.0 and about 1.2 moles per mole of halobenzene sulfonyl halide. More aluminum trichloride can be used than the upper limit of 1.2 moles/mole HBSH, but no significant advantage is to be gained and the cost of making the product disadvantageously rises. An amount of aluminum trichloride in excess of about 2 moles/mole HBSH also results in product color deterioration.

Ferric chloride has been tried as a Friedel-Crafts catalyst in this invention, but has been found, generally, relative to using single component solvents, not to produce increased yield of disulfone monomer beyond those within the limits of experimental error.

The manner of combining reactants is not critical. Solvent and catalyst, optionally together with one of the reactants, may be combined and all or the remaining reactant, dissolved in additional solvent, added thereto as from a dropping funnel. Alternatively the reactants may be dissolved in the solvent and the catalyst, suspended in additional solvent, dropped therein. The total volume of solvent, once all reactants and catalyst have been combined, should not exceed that amount which provides between about 0.5 and about 1.5 moles of nitromethane per mole of catalyst.

The reaction temperature should vary between about 50° and about 130° C., preferably between about 85° and about 115° C. At temperature much above 130° C. thermal degradation and tarring becomes likely.

Generally an inert gas (helium, nitrogen, argon, etc.) sparge should be implemented to remove hydrogen halide (e.g., HCl) as it is formed during the reaction. The gaseous effluent can be implemented to pass through a solution of base such as an alkali metal hydroxide or carbonate to neutralize the acid.

Mechanical agitation should also be implemented as by employing a mechanical or magnetic stirrer to ensure good mixing.

Reaction duration can vary widely depending on the particular solvent components, solvent composition, temperature, and specific reactants employed, but will typically vary from about 1 to about 24 hours. The product solution is a homogeneous solution containing not only the desired disulfone compound, but also the half reacted (monosulfone) compound as well, wherein the sulfone groups are complexed with dissolved catalyst. At this point, a quenching agent may be added to fracture the sulfone/catalyst complex. Preferred as quenchant is a methanol/water solution having a ratio (V/V) of methanol to water varying from 0/100 to 100/0, i.e. pure methanol or pure water may be desired in some cases. The optimum quench composition for a given synthesis is determined according to solvent composition and the desire to avoid obtaining the product as an oil or creating an emulsion. The optimum quench composition can be facilely determined by making trial runs.

Quenching yields a two-phase solution wherein the lower phase is generally organic and contains the desired disulfone product. Depending on the particular disulfone product, reaction solvent composition, and quench composition the product may be a solid powder or oil. The phase containing the desired product is isolated (as by being drawn off from a separatory funnel) and the product, if a powder, is isolated by filtration. If an oily product is obtained, it may be isolated as the oil and then added to pure methanol to induce crystallization. Recrystallization from common recrystallization solvents such as dimethylformamide orthodichlorobenzene, or cyclohexanone typically gives yields in excess of 70% of theoretical following recycle.

The liquid left after filtration of or oil separation from the quench phase initially containing the product, and the recrystallization mother liquor, should each be evaporated to recover any monosulfone compound (i.e. the compound which is only half substituted and which has the formula X-Ph-SO$_2$-Q-H wherein Ph=phenyl and X and Q are as previously defined), the residue following evaporation being taken up in fresh mixed solvent and recycled to the reactor.

EXAMPLES

EXAMPLE 1

In a 1 liter 3-neck flask equipped with a mechanical stirrer, nitrogen sparge tube, dropping funnel, thermometer, and reflux condenser (two claisen adapters for a total of 5-necks were needed to assemble the apparatus) were put 12 ml of nitromethane and 68 ml of 1,2-dichloroethane. To this solution were added 34.61 g (0.26 moles) of AlCl$_3$. Next, 50 g (0.24 moles) of pCBSC and 15.48 g (0.10 moles) of biphenyl were added to the solution. The solution immediately turned a dark burgundy upon addition of biphenyl. The N$_2$ sparge was immediately applied and heat was applied to achieve reflux. After 30 minutes the reaction mixture was a deep burgundy (temp. approximately 90° C.). Due to solvent evaporation, at this point an additional 6 ml of nitromethane and 34 ml of dichloroethane were slowly added to the reaction mixture (over 45 min.), although additional mixed solvent need not normally be added when efficient condensers are employed. After an additional 4 hours when the reaction was judged complete due to no additional HCl evolution, the heat was turned off and the reaction was allowed to cool for approximately 30 minutes. The mixture was then cooled to 10° C. and 300 ml of a 2/1:v/v solution of CH$_3$OH/H$_2$O were added over 10 minutes to the reaction mixture. At this point the heating mantle was replaced and the solution was refluxed for 45 minutes, allowed to cool, and filtered. Yield 74% mp 257-267 (expect 272°-257° C.).

EXAMPLE 2

A reaction was conducted as in Example 1, with the following modifications:
1. The solvent used consisted of 12 ml of nitromethane and 125 ml of 1,2-dichloroethane;
2. terphenyl was substituted for biphenyl in the same molar amount;
3. More efficient solvent condensers were employed, thus essentially no solvent loss occurred during reflux and no makeup solvent was needed.

After conducting the reaction for approximately 5 hours at reflux, a crude (i.e. preceding recrystallization) yield of approximately 90% was obtained.

EXAMPLE 3

A reaction was conducted as in Example 1, with the following modifications:
1. The solvent consisted of 12 ml of nitromethane and 100 ml of 1,2-dichloroethane;
2. 26 g of terphenyl was substituted for biphenyl;
3. 45.5 g of p-fluorobenzenesulfonyl chloride was substituted for pCBSC;
4. Efficient solvent condensers were employed as in Example 2.

The reaction was conducted at reflux for 5 hrs, a crude yield of about 74% being obtained.

EXAMPLE 4

The following example is comparative and shows the less desirable results achieved using neat aliphatic halohydrocarbon as a solvent in lieu of the mixed solvent system of Examples 1-3.

In a 3-neck flask with reflux condensor, thermometer, mechanical stirrer, N₂ inlet tube, and dropping funnel was put 50 g of para-chlorobenzene sulfonyl chloride, 15.5 g of biphenyl, 34.6 g of AlCl₃, and 80 ml of 1,2-dichloroethane. The reaction was then heated to reflux and maintained at that temperature for 4 hours. The reaction solution was cooled, then 100 ml of methanol followed by 100 ml of 10% aqueous HCl solution were added. The powdered product was filtered to give a relatively dark brown substance, considerably darker than that obtained using CH₃NO₂ as a cosolvent.

EXAMPLE 5

The following example is comparative and shows the less desirable results achieved using an aromatic halohydrocarbon as a mixed solvent component.

An apparatus was assembled as described in Example 1 and equipped with a thermostat to provide temperature control. 200 g of pCBSC, 62 g of biphenyl, 138.4 g of aluminum trichloride, 53.4 ml of nitromethane, and 300 ml of orthodichlorobenzene (DCB) were added into the apparatus. The reaction mixture was heated to 100° C. and maintained at that temperature for 4.5 hours. At this point the reaction was allowed to cool and was then poured into a mixture of 500 ml of methanol and 250 ml of water. The product disulfone compound was in the DCB layer, which layer was separated. Addition of 1 liter of methanol induced crystallization of the product. The product was yellowish brown, having color quality considerably poorer than that for the same compound obtained using pure DCB as the solvent.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A process for producing dihalobenzene disulfone compounds which consists essentially of reacting, in the presence of a catalytic amount aluminum trichloride a halobenzene sulfonyl halide of the formula

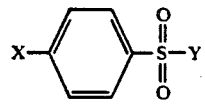

wherein X and Y are halogen which may be the same or different, with a compound of the formula

HQH where Q is selected from the group consisting of biphenylene and terphenylene; in a solvent consisting essentially of about 1 to about 25 volume percent of nitromethane, and of about 99 to about 75 volume percent based on the total volume of solvent of 1,2-dichloroethane; the total amount of solvent being such that from about 0.5 to about 1.5 moles of nitromethane are provided for each mole of aluminum trichloride.

2. A process as defined in claim 1, wherein said halobenzene sulfonyl halide is p-chlorobenzene sulfonyl chloride or p-fluorobenzene sulfonyl chloride.

3. A process as defined in claim 1, wherein said reaction is conducted at a temperature between about 50° C. and about 130° C.

4. A process as defined in claim 1, wherein said temperature is between about 85° C. and about 115° C.

5. A process as defined in claim 1, wherein the amount of nitromethane is between about 0.75 and about 1.25 moles per mole of aluminum trichloride.

6. A process as defined in claim 1, wherein said amount of nitromethane is between about 0.85 and about 1.05 moles per mole of aluminum trichloride.

* * * * *